United States Patent [19]
Chassaing et al.

[11] Patent Number: 6,080,724
[45] Date of Patent: Jun. 27, 2000

[54] PEPTIDES WHICH CAN BE USED AS VECTORS FOR THE INTRACELLULAR ADDRESSING OF ACTIVE MOLECULES

[75] Inventors: Gérard Chassaing; Alain Prochiantz, both of Paris, France

[73] Assignee: Centre National de la Recherche Scientifique (CNRS), Paris, France

[21] Appl. No.: 08/849,486

[22] PCT Filed: Oct. 4, 1996

[86] PCT No.: PCT/FR96/01553

§ 371 Date: Jun. 5, 1997

§ 102(e) Date: Jun. 5, 1997

[87] PCT Pub. No.: WO97/12912

PCT Pub. Date: Apr. 10, 1997

[30] Foreign Application Priority Data

Oct. 5, 1995 [FR] France .................................. 95 11714

[51] Int. Cl.[7] .................................................. A61K 38/00
[52] U.S. Cl. ............................................ 514/13; 530/326
[58] Field of Search ................................ 530/326; 514/13

[56] References Cited

U.S. PATENT DOCUMENTS

| | | | |
|---|---|---|---|
| 5,015,571 | 5/1991 | Niman et al. | 435/7.92 |
| 5,563,247 | 10/1996 | Niman et al. | 530/387.7 |
| 5,846,722 | 12/1998 | Kauvar et al. | 435/6 |
| 5,877,282 | 3/1999 | Nadler et al. | 530/350 |
| 5,888,762 | 3/1999 | Joliot et al. | 435/69.1 |

OTHER PUBLICATIONS

Derossi, D. et al., *The Third Helix of the Antennapedia Homeodomain Translocates through Biological Membranes*, The Journal of Biological Chemistry, vol. 269, No. 14, Apr. 8, 1994, pp. 10444–10450.

Le Roux, I. et al., *Neurotrophic activity of the Antennapedia homeodomain depends on its specific DNA–binding properties*, Proceedings of the National Academy of Sciences of USA, vol. 90, No. 19, Oct. 1, 1993, pp. 9120–9194.

Derossi, D. et al., *Cell Internalization of the Third Helix of the Antennapedia Homeodomain Is Recepter–independent*, The Journal of Biological Chemistry, vol. 271, No. 30, Jul. 26, 1996, pp. 18188–18193.

Boersch–Supan, *J. Exp. Med.*, 161(6), 1272–92, 1985.
Caplus DN 120:104735, Pelfrey et al., J. Neuroimmunol., 46(1–2), 33–42 (abstract), 1973.
Caplus DN 107:232980, Tallon et al., *Biochemistry*, 26(24), 7767–74, (abstract), 1987.
Caplus DN 106:171491, Voges et al., *Biochim. Biophys. Acta*, 896(1), 64–76 (abstract), 1987.
Caplus DN 105:41064, Niman et al., WO 8500807 A1. (abstract), 1985.
Caplus DN 119:160797, Calmes et al., *Tetrahedron Lett.*, 34(20), 3275–8. (abstract), 1993.
Caplus DN 111:35190, Daumas et al., *Biochimie*, 71(1), 77–81. (abstract), 1989.
Caplus DN 112:199069, Hunt et al., *Anal. Chim. Acta*, 225(1), 1–10. (abstract), 1989.
Boersch–Supan. *J. Exp. Med.*, 161(6), 1272–92, 1985.
Derossi et al., *The Journal of Biological Chemistry*, vol. 269, No. 14, pp. 10444–10450, 1994.

*Primary Examiner*—Dwayne C. Jones
*Assistant Examiner*—C. Delacroix-Muirheid
*Attorney, Agent, or Firm*—Alston & Bird LLP

[57] ABSTRACT

The invention relates to a peptide of sequence (I) or (Ia):

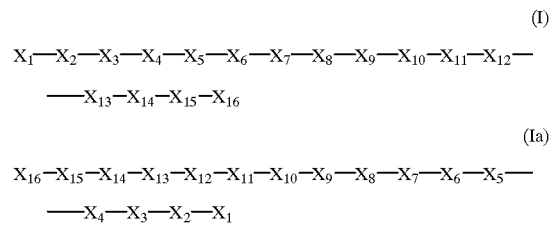

where $X_1$, $X_2$, $X_3$, $X_4$, $X_5$, $X_7$, $X_8$, $X_9$, $X_{10}$, $X_{11}$, $X_{12}$, $X_{13}$, $X_{14}$, $X_{15}$, $X_{16}$ each represent an α-amino acid, $X_6$ representing tryptophan. This peptide comprises between 6 and 10 hydrophobic amino acids.

The invention also relates to the use of the said peptide for introducing, into living cells, a molecule which is active on the cellular functions.

25 Claims, 6 Drawing Sheets

PEPTIDES WHICH CAN BE USED AS VECTORS FOR THE INTRACELLULAR ADDRESSING OF ACTIVE MOLECULES

This application is a 371 of PCT/FR96/01553, filed Oct. 4, 1996.

FIELD OF THE INVENTION

The present invention relates to a class of peptides capable of crossing the cellular membranes and of reaching the various compartments of the cell.

BACKGROUND OF THE INVENTION

The problem of the entry, into living cells, of various substances having pharmacological properties, and of their access to the various intracellular compartments, in particular the cytoplasmic compartment and the nuclear compartment, is of great importance both for research and for therapeutic use.

A limited number of means for introducing substances such as polypeptides and oligonucleotides into the intracellular compartments is currently known. Among the various techniques currently proposed, there may be mentioned:

1. The transfection of genes, and derived techniques which make it possible to enhance in vivo or in vitro the transfection rates, such as precipitation with calcium phosphate, the use of cationic lipids, electroporation, trituration (scrape loading), the use of viral vectors, and the like.

2. The binding to cellular membrane receptors; these receptors are subsequently endocytozed, and release the bound molecules into the cytoplasmic compartment. In this category, there may be mentioned the folate receptor, the diphtheria toxin or transcription factors such as the TAT protein of the HIV retrovirus. The mechanism of transport involving these receptors is still poorly known, but requires in all cases an endocytosis stage.

3. The homeodomain-type peptides. Previous work carried out by the team of inventors on the homeodomain of the transcription factor Antennapedia (AntpHD) have made it possible to show that the homeodomain peptides cross the plasma membranes by an energy-independent process which is therefore distinct from endocytosis. The 3rd helix of the homeodomain peptide has the same properties [JOLIOT et al., Proc. Natl. Acad. Sci., USA, 88, p. 1864–1868 (1991); DEROSSI et al., J. Biol. Chem. 269, 14, p. 10444–10450, (1994)].

These properties have been used to internalize, in cells, polypeptides and oligonucleotides linked to the homeodomain or to helix 3, [PEREZ et al., J. Cell. Science, 102, p. 712–722, (1992)] by genetic fusion or biochemical bonding. This entry is quantitative, and the vector and its load are found in 100% of the cells; in addition, the internalization is independent of the relevant cell type.

The smallest fragment of the homeodomain capable of crossing the membranes and of serving as vector for other peptides or for oligonucleotides is a peptide of 16 amino acids, corresponding to helix 3. This peptide, which comprises amino acids 43 to 58 of the homeodomain, is named below. By way of example, the sequence of the peptide 43-58 of the homeodomain Antp is the following:

Arg-Gln-Ile-Lys-Ile-Trp-Phe-Gln-Asn-Arg-Met-Lys-Trp-Lys-Lys

This sequence is represented in the sequence listing in the annex under the number SEQ ID NO:1.

The mechanism by which this peptide could penetrate into living cells has been the subject of various studies, and it was assumed until now that its alpha-helix structure was essential for the internalization. The team of inventors has previously shown that certain substitutions or deletions in the peptide sequence, which modified the structure of the peptide, interfered with the activity of the said peptide. For example, a peptide in which the 2 Trp's (48 and 56) are replaced by two Phe's, or a peptide comprising amino acids 41 to 55 of the homeodomain are not internalized (DEROSSI et al., 1994, publication cited above). Another team [BRUGIDOU et al., Biophys. Biochem. Res. Com., 214:2, pp 685–693, (1995)] observed the internalization of peptides constituting structural analogues of the peptide 43-58; for that, they constructed, from a peptide 43-58 (differing from the peptide 43-58 of the homeodomain Antp in that the 2 isoleucines at positions 45 and 47 are replaced by valines), variants of the retro-inverse type. The retro-inverse variants, which make it possible to mimic the three-dimensional structure of natural peptides, consist of amino acids of the D series (instead of amino acids of the L series in the natural peptides) linked according to a sequence which is the reverse of that of the peptide to be reproduced.

The inventors have now sought to define the minimum characteristics of the amino acid sequences capable of serving as vector for the internalization and addressing of polypeptides and oligonucleotides, and have, for this purpose, synthesized several peptides by specifically modifying certain residues.

SUMMARY OF THE INVENTION

The subject of the present invention is a peptide corresponding to one of the following sequences (I) or (Ia):

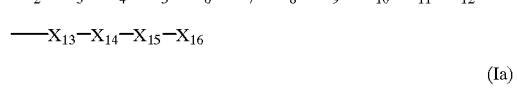

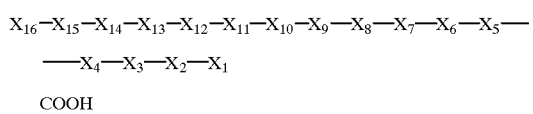

where $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$ each represent an α-amino acid, which peptide is characterized in that it comprises between 6 and 10 hydrophobic amino acids, and in that $X_6$ represents tryptophan, with the exception of the following peptides:

the peptide whose sequence is represented in the sequence listing in the annex under the number SEQ ID NO:1;

the peptides in which $X_3$ and $X_5$ each represent a valine residue.

The hydrophobic amino acids are alanine, valine, leucine, isoleucine, proline, phenylalanine, tryptophan and methionine.

The rest of the amino acids which enter into the constitution of the peptides in accordance with the invention are non-hydrophobic amino acids which may be polar amino acids (glycine, serine, threonine, cysteine, tyrosine, asparagine, glutamine), acidic amino acids (aspartic or glutamic acid) or basic amino acids (lysine, arginine or histidine), or a combination of amino acids of these three categories.

According to a preferred embodiment of a peptide in accordance with the invention, it comprises 6 hydrophobic amino acids and 10 non-hydrophobic amino acids.

The linkage of polar or charged non-hydrophobic amino acids, and of hydrophobic amino acids confers on the peptides in accordance with the invention an amphiphilic character which, according to the experiments carried out by the inventors, appears to be essential for their properties. These experiments have, in addition, made it possible to highlight other characteristics essential for intracellular translocation, and to show that:

intracellular translocation does not require a specific receptor, and can therefore affect all cellular types;

the alpha-helix structure does not play a part in intracellular translocation, (but undoubtedly plays a role in nuclear addressing);

the amphiphilic properties of the peptide, as well as the presence of a Trp residue appear, on the other hand, to be important for translocation.

Preferably, a peptide in accordance with the invention consists of sequences comprising from 1 to 6 non-hydrophobic amino acids and from 1 to 6 hydrophobic amino acids, alternately distributed along the peptide chain.

According to another embodiment of a peptide in accordance with the invention, $X_1$, $X_2$, $X_4$, $X_9$, $X_{15}$ and $X_{16}$ are non-hydrophobic amino acids and $X_3$, $X_7$ and $X_{14}$ are hydrophobic amino acids. According to a preferred feature of this embodiment, $X_{14}$ represents tryptophan or isoleucine.

The intracellular penetration properties of the peptides in accordance with the invention are comparable to those of helix 3 of a homeodomain peptide, and allow their use as internalization and intracellular addressing vector for introducing, into living cells, molecules which are active on the cellular functions, in particular other peptides or nucleotide sequences.

To obtain an addressing, which is more specifically cytoplasmic, of the active molecule which it is desired to introduce, a peptide in accordance with the invention in which at least one of the amino acids in position $X_3$, $X_7$ and $X_{14}$ is a proline, will be preferably used.

For the implementation of the present invention, the polypeptide or oligonucleotide to be transported is bound to a peptide in accordance with the invention.

The products of fusion of a peptide in accordance with the invention with another peptide sequence, or with an oligonucleotide sequence may be obtained by different means known per se. In the case of a polypeptide, conventional genetic engineering or peptide synthesis techniques may be used for example. In the case of an oligonucleotide, there may be used, for example, the technique described by LEMAITRE et al. [Proc. Natl. Acad. Sci. USA, 84, 648–652, (1987)], or that of MATSUEDA et al. [Chemistry Letters, p. 951–952, (1978) and Int. J. of Peptide and Protein Research, p. 107–112 (1986)].

BRIEF DESCRIPTION OF THE DRAWINGS

FIG. 2 shows that the labeled peptides have been internalized into the cells. E15 embryonic cortex cells were incubated at 4° C. in culture medium having biotin labeled peptides. After the incubation, the culture medium was collected. The cells were washed with trypsin. The presence of the labeled peptides the cells was then tested by SDS-PAGE gel electrophoresis.

(FIG. 5A) and 4° C. (FIG. 5B).

DETAILED DESCRIPTION OF THE INVENTION

Figure 1:
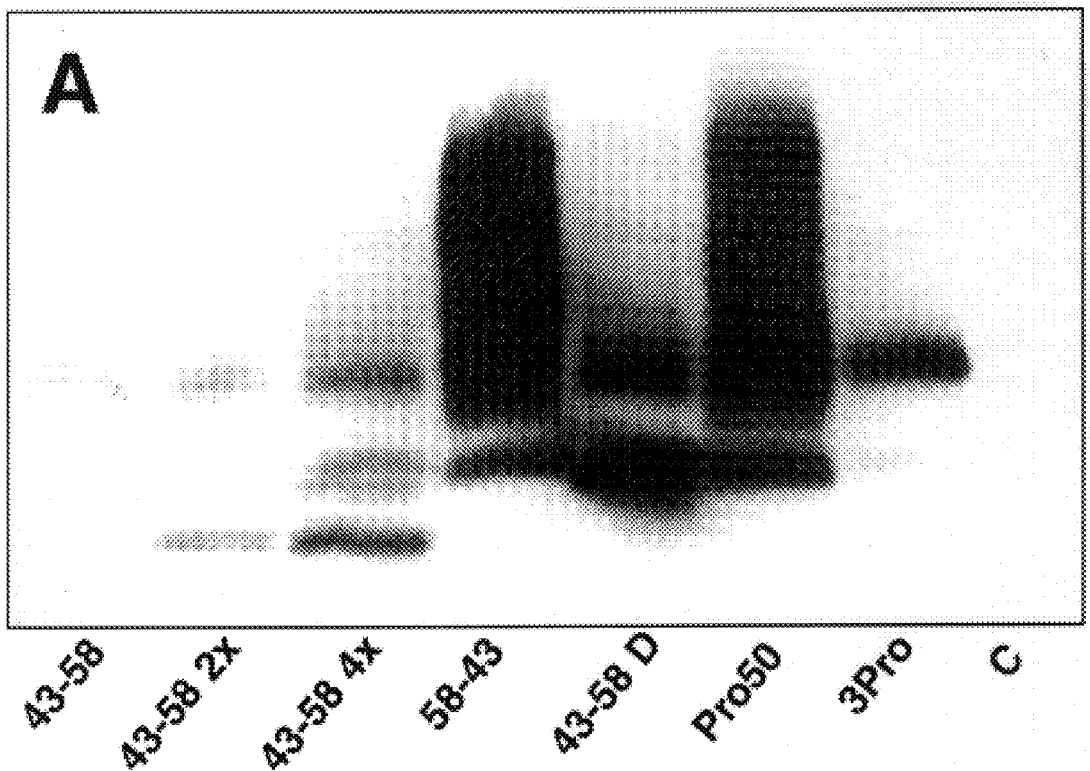
FIGS. 1(A and B) is a bioluminescence autoragram gel electrophoresis of cell extracts (FIG. 1A) obtained from cells incubated with labeled peptides indicated in Table I, and gel electrophoresis of the incubation medium (FIG. 1B) evidencing the presence of labeled peptides within the cells. E15 embryonic cortex cells were incubated at 37° C. in culture medium having biotin labeled peptides. After the incubation, the culture medium was collected. The cells were washed with trypsin. The presence of the labeled peptides in culture medium and the cells was then analyzed by SDS-PAGE gel electrophoresis.
Figure 1:
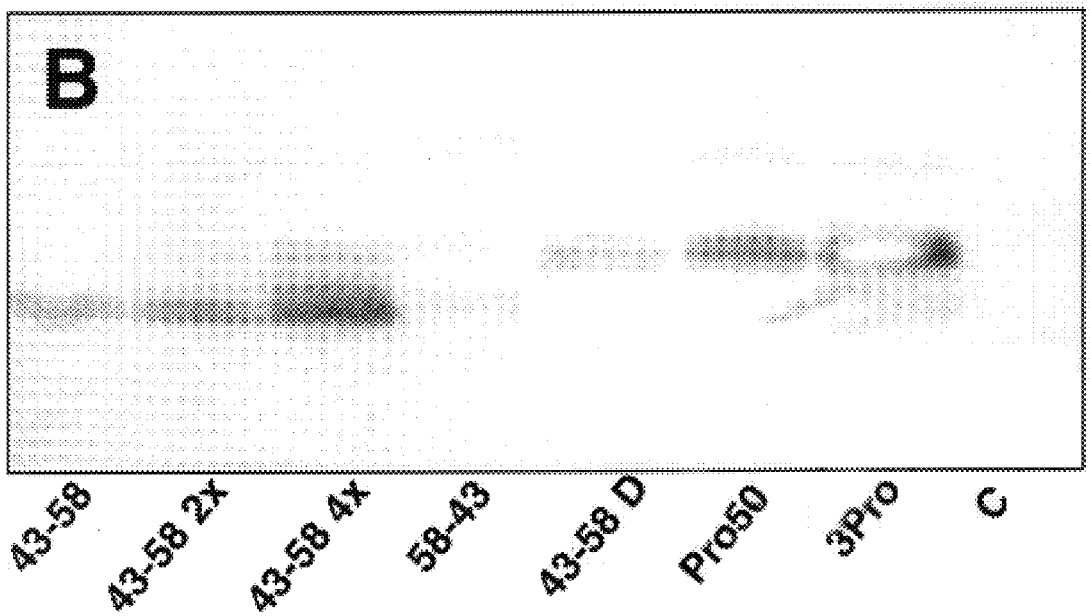

The present invention will be understood more clearly with the aid of the additional description which follows, which refers to an example showing the properties of various peptides in accordance with the invention.

It should be understood, however, that this example is given solely by way of illustration of the subject of the invention and does not in any manner constitute a limitation thereto.

EXAMPLE 10 peptides, whose sequences are represented in the sequence listing in the annex under the numbers SEQ ID NO:1 to SEQ ID NO:10 were synthesized. All these peptides were, in addition, provided at their N-terminal end with an aminopentanoic arm and a biotin allowing their internalization to be monitored; the peptides thus modified are represented in Tables I and II below.

Table I

| | 43–58 | |
|---|---|---|
| Biot-Apa-Arg-Gln-Ile-Lys-Ile-Trp-Phe-Gln-Asn-Arg-Arg-Met-Lys-Trp-Lys-Lys | | SEQ ID NO:1 |
| | 41–55 | |
| Biot-Apa-Thr-Glu-Arg-Gln-Ile-Lys-Ile-Trp-Phe-Gln-Asn-Arg-Arg-Met-Lys | | SEQ ID NO:2 |
| | 58–43 | |
| Biot-Apa-Lys-Lys-Trp-Lys-Met-Arg-Arg-Asn-Gln-Phe-Trp-Ile-Lys-Ile-Gln-Arg | | SEQ ID NO:3 |
| | 43–58 D | |
| Biot-Apa-Arg-Gln-Ile-Lys-Ile-Trp-Phe-Gln-Asn-Arg-Arg-Met-Lys-Trp-Lys-Lys | | SEQ ID NO:4 |
| | Pro50 | |
| Biot-Apa-Arg-Gln-Ile-Lys-Ile-Trp-Phe-<u>Pro</u>-Asn-Arg-Arg-Met-Lys-Trp-Lys-Lys | | SEQ ID NO:5 |
| | 3Pro | |
| Biot-Apa-Arg-Gln-<u>Pro</u>-Lys-Ile-Trp-Phe-<u>Pro</u>-Asn-Arg-Arg-Lys-<u>Pro</u>-Trp-Lys-Lys | | SEQ ID NO:6 |

Table II

| | Met-Arg | |
|---|---|---|
| Biot-Apa-Arg-Gln-Ile-Lys-Ile-Trp-Phe-Gln-Asn-Met-Arg-Arg-Lys-Trp-Lys-Lys | | SEQ ID NO:7 |
| | 7Arg | |
| Biot-Apa-Arg-Gln-Ile-Lys-Ile-Trp-Phe-Gln-Asn-Arg-Arg-Met-Arg-Trp-Arg-Arg | | SEQ ID NO:8 |
| | W/R | |
| Biot-Apa-Arg-Arg-Trp-Arg-Arg-Trp-Trp-Arg-Arg-Trp-Trp-Arg-Arg-Trp-Arg-Arg | | SEQ ID NO:9 |
| | LR/ | |
| Biot-Apa-Arg-Leu-Arg-Arg-Leu-Leu-Arg-Arg-Leu-Leu-Arg-Arg-Leu-Arg-Arg | | SEQ ID NO:10 |

Legend to Table I 43-58: Peptide helix 3rd 41-55: Control: Non-internalized peptide (see DEROSSI et al., 1994)

58-43: Reverse sequence 43-58 D: Peptide 3rd helix (43-58) consisting of amino acids of the D series Pro50: Peptide 43-58 with a Proline in 50 (instead of Gln)

3Pro: Peptide 43-58 with 3 Prolines at positions 45, 50 and 55, in place of the Ile, Gln and Lys residues respectively.

Legend to Table II

Met-Arg: Peptide 43-58 with Met in 52 (instead of Arg) and Arg in 54 (instead of Met)

7Arg: All the Lysines of the peptide 43-58, except that in 46 are replaced with Arg's W/R: Peptide 43-58 highly modified, consists essentially of a succession of Trp and Arg L/R: Peptide W/R with Leu's in place of Trp's.

The entry of these various peptides into cells in culture was studied under the same conditions and using the same procedures as those described by DEROSSI et al. (1994, publication cited above).

The entry of the peptides into the nerve cells or fibroblasts in culture was examined at 4 and 37° C.

The entry of the peptides of Table I was tested by confocal microscopy, gel electrophoresis and ELISA.

The entry of the peptides of Table II was tested only by confocal microscopy; indeed, the absence of lysine in these peptides makes the attachments very difficult and therefore requires a very rapid observation which is incompatible with transfers onto filters or ELISA tests (multiple washes).

1) Internalization at 37° C. and at 4° C. of the peptides 43-58, 58-43, D43-58, Pro50 and 3Pro E15 embryonic cortex cells were incubated ($1.1 \times 10^6$ cells/ml) for 2 h at 37° C. or at 4° C. with the peptides 43-58, 58-43, D43-58, Pro50 and 3Pro, at the concentration of 44 $\mu$M for a quantity 1X, or without peptide (well C).

The presence of the peptides in the incubation medium and in the cells after washing them with trypsin was analysed on a 12–22% SDS-PAGE electrophoresis gel and by electrotransfer.

The results are illustrated in FIGS. 1A, 1B (37° C.) and 2 (4° C.).

Legend to FIG. 1:

A: Autoradiogram of the cellular extracts after revealing by bioluminescence (LUMINOL®, AMERSHAM).

B: Autoradiogram of the incubation media after revealing by bioluminescence.

Figure 2:
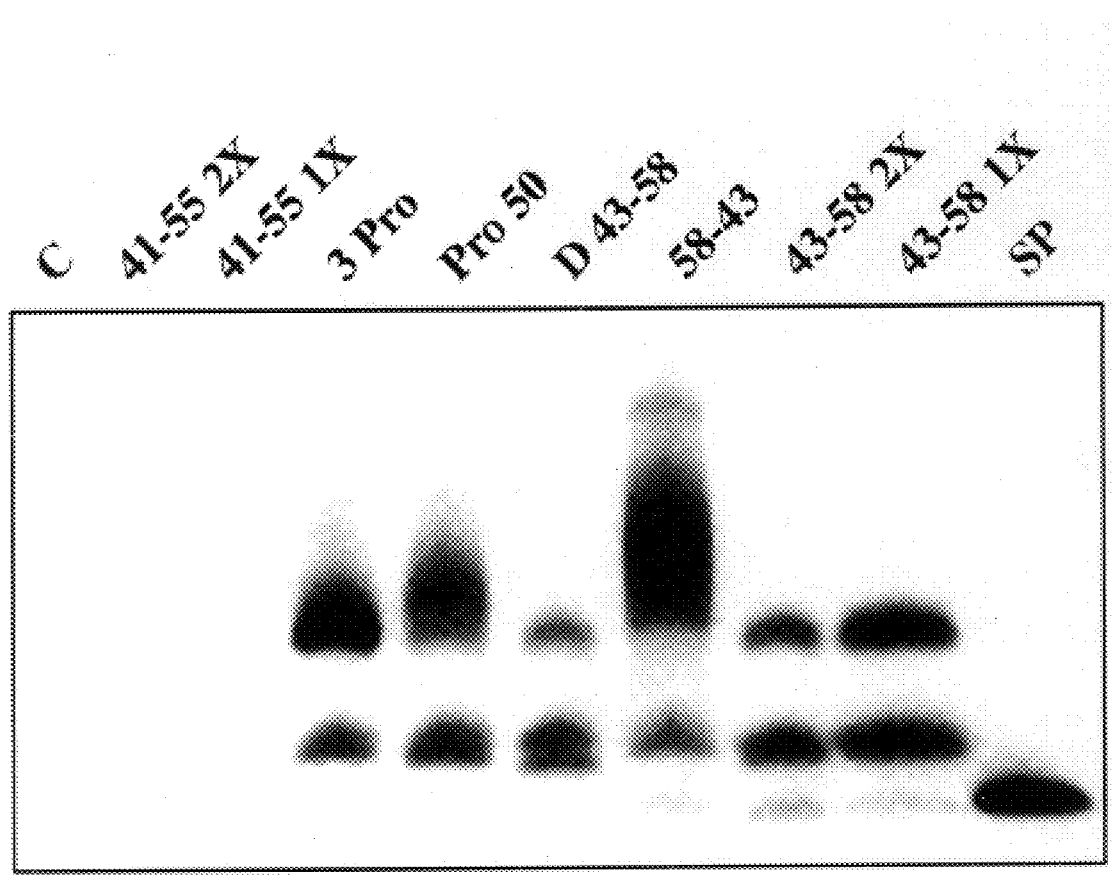
FIG. 2 is a bioluminescence autoragram gel electrophoresis of cell extracts obtained from cells incubated with labeled peptides indicated in Table I.

Legend to FIG. 2:

The well SP corresponds to the loading onto the gel of 1 $\mu$l of substance P.

All the peptides of Table I, with the exception of 41-55, are internalized at 4 and 37° C. and recovered in the cells. The peptide 43-58 is degraded (about 50%) at 37° C. but not at 4° C.

2) Cellular localization of the peptides 43-58, 51-55, 58-43, D43-58, Pro50 and 3Pro at 37° C. and 4° C.

The E15 cortex and striatum cells are cultured on glass coverslips at a density of 25,000 cells/cm² for 2 days. The peptides are all added at a final concentration of 20 $\mu$M. After 2 h of incubation at 37° C., the cells are washed, fixed and the presence of biotin is revealed by fluorescent streptavidin. The sections observed by confocal microscopy are presented in FIGS. 3 (37° C.) and 4 (4° C.). The cells which have integrated the peptide appear fluorescent, on a black background.

Figure 3:
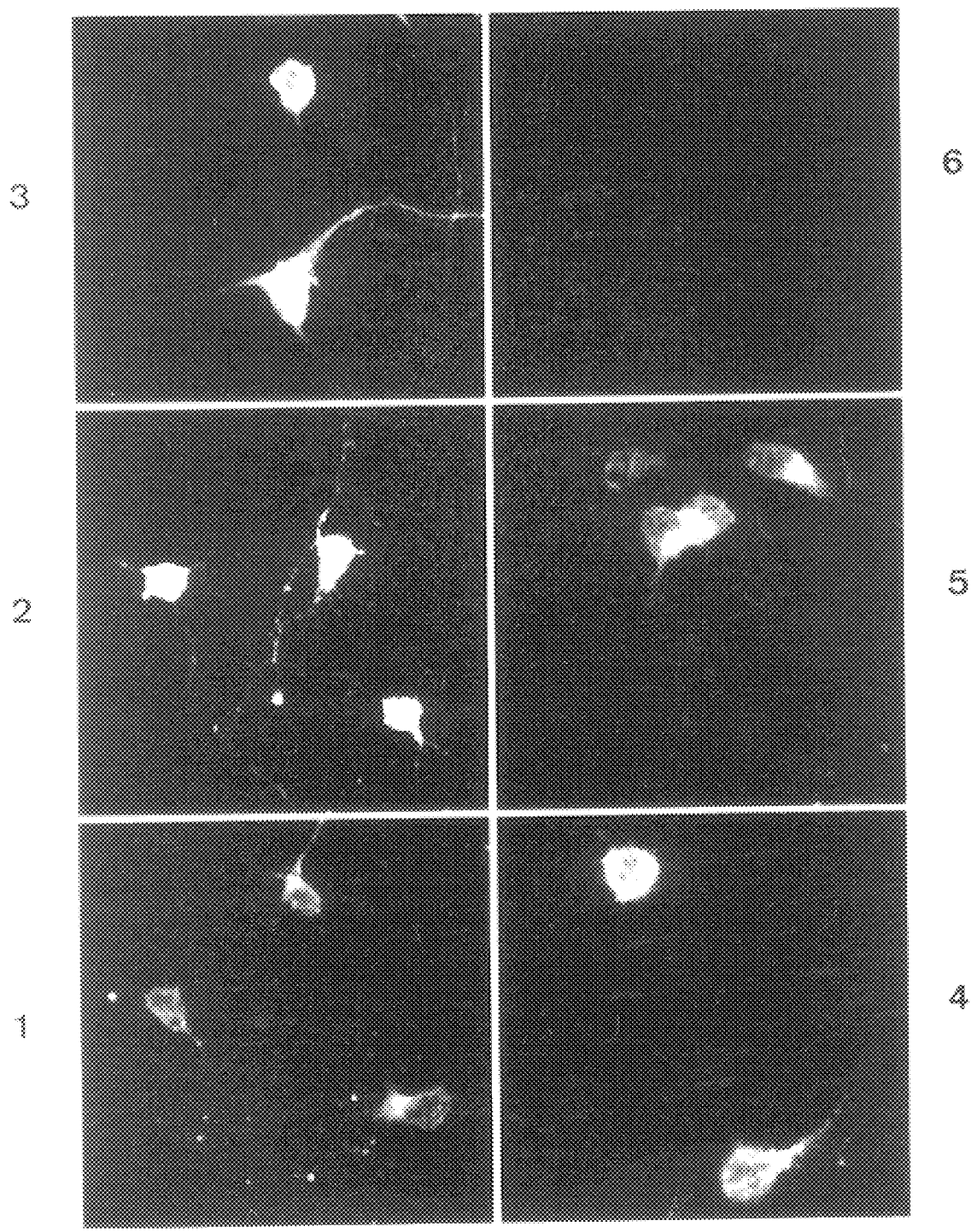
FIG. 3 shows the cell images under confocal microscopy indicating the presence of labeled peptides within the cells. The E15 cortex and striatum cells were incubated at 37° C. in culture medium having biotin labeled peptides to allow the peptides to internalize into the cells. The cells were then washed, fixed and stained with fluorescent streptavidin.

Legend to FIG. 3:

1: peptide 43–58,    2: peptide 58–43,
3: peptide D43–58,    4: peptide Pro50,
5: peptide 3Pro,    6: peptide 41–55.

Figure 4:
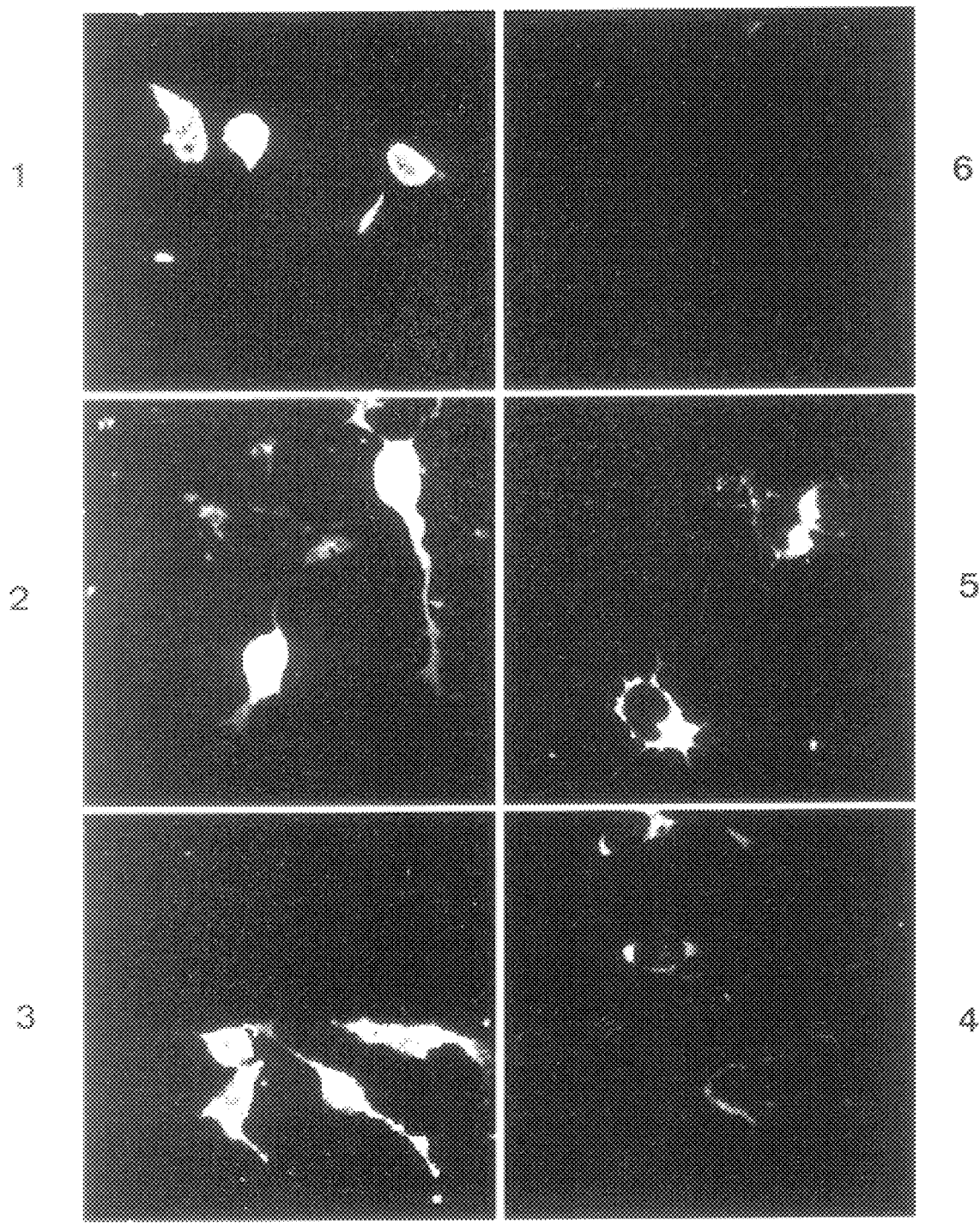
FIG. 4 shows the cell images under confocal microscopy indicating the presence of labeled peptides within the cells. The E15 cortex and striatum cells were incubated at 4° C. in culture medium having biotin labeled peptides to allow the peptides to internalize into the cells. The cells were then washed, fixed and stained with fluorescent streptavidin.

Legend to FIG. 4:

1: peptide 43–58,    2: peptide 58–43,
3: peptide D43–58,    4: peptide Pro50,
5: peptide 3Pro,    6: peptide 41–55.

The presence of prolines (Pro50 or 3Pro) does not prevent internalization but appears to interfere with nuclear addressing. The entry of the peptides tested is also observed in fibroblasts (not shown).

3) Colorimetric assay of the internalizations of the peptides 43-58, 51-55, 58-43, D43-58, Pro50 and 3Pro at 37° C. and 4° C.

E15 (B) or E16 (A) cortex and striatum cells were incubated ($1.1 \times 10^6$ cells/ml) with peptides at a concentration of 17 µM (A) or 44 µM (B) for quantities 1X, or without peptides (9). The cells were washed with 0.5 M NaCl (A) or with trypsin (B). They were cultured on ELISA plate, fixed and biotinylated peptides were revealed using a coloured substrate (PNPP) of alkaline phosphatase coupled to streptavidin.

Figure 5:
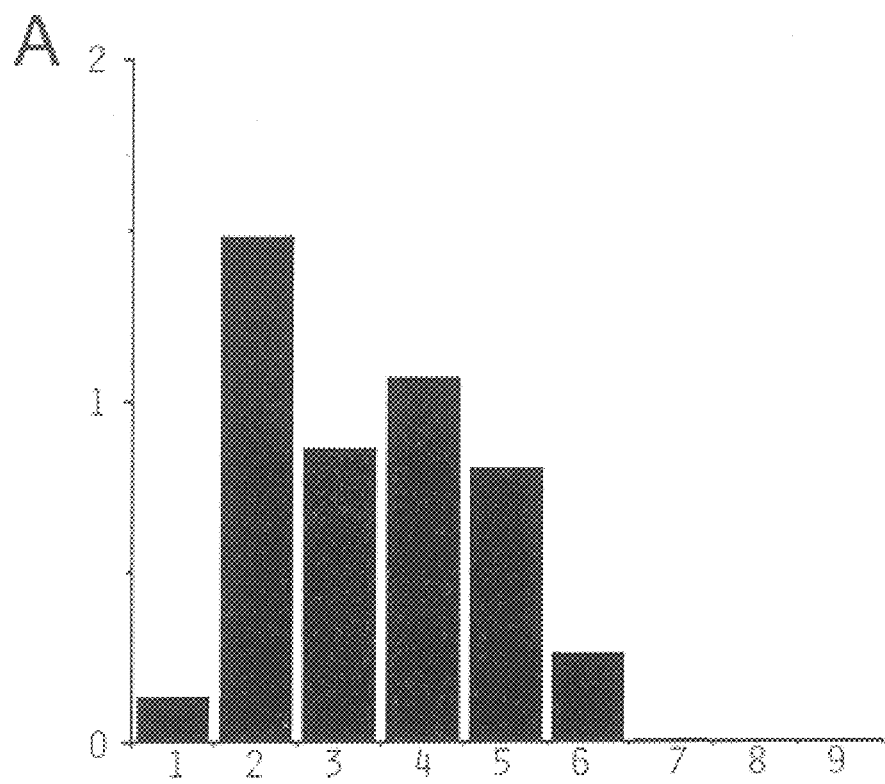
FIGS. 5(A and B) demonstrate in diagrams the calorimetric assay results of the internalizations of the peptides 43-58, 51-55, 58-43, D43-58, Pro50 and 3Pro at 37° C.
Figure 5:
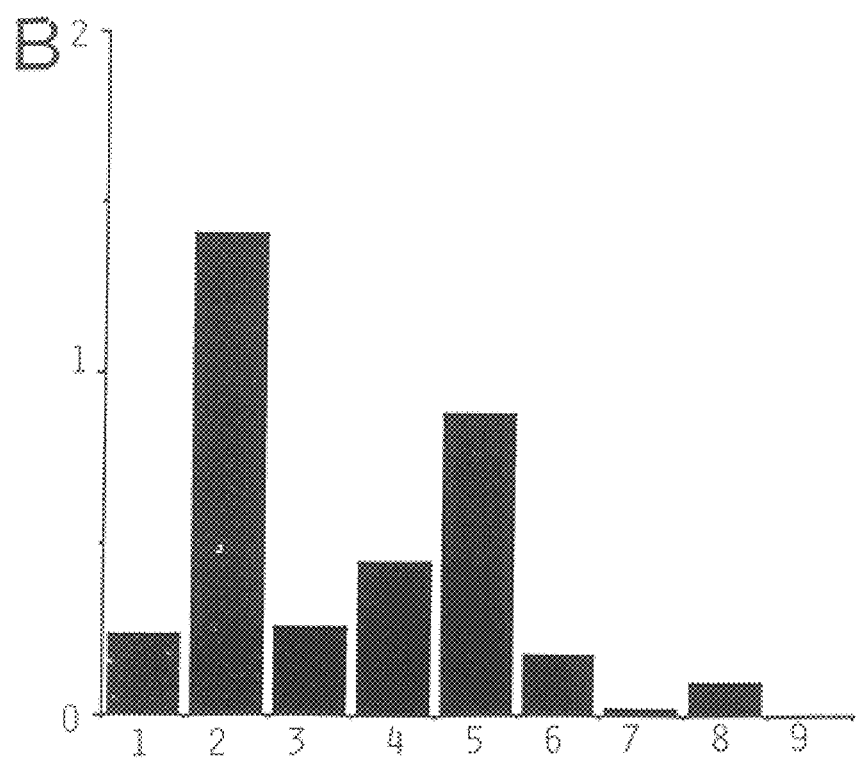

The results are illustrated in FIGS. 5A and 5B.

Legend to FIGS. 5A and 5B:

A: experiment at 37° C.;
B: experiment at 4° C.

1: peptide 43-58 1X
2: peptide 43-58 4X
3: peptide 58-43 1X
4: peptide D43-58
5: peptide Pro50
6: peptide 3Pro
7: peptide 41-55 1X
8: peptide 41-55 4X, sample not present in A
9: no peptide.

4) Internalization at 37° C. of the peptides Met-Arg, W/R and L/R

E15 cortex and striatum cells are cultured on glass coverslips at a density of 25,000 cells/cm² for 2 days. The peptides are added at a final concentration of 20 µM for peptide 43-58 and of 2 µM for the others and the cells are incubated for 2 h at 37° C. The cells are washed, fixed and the biotin of the peptides is revealed by streptavidin-FITC. The results are illustrated in FIG. 6.

Figure 6:
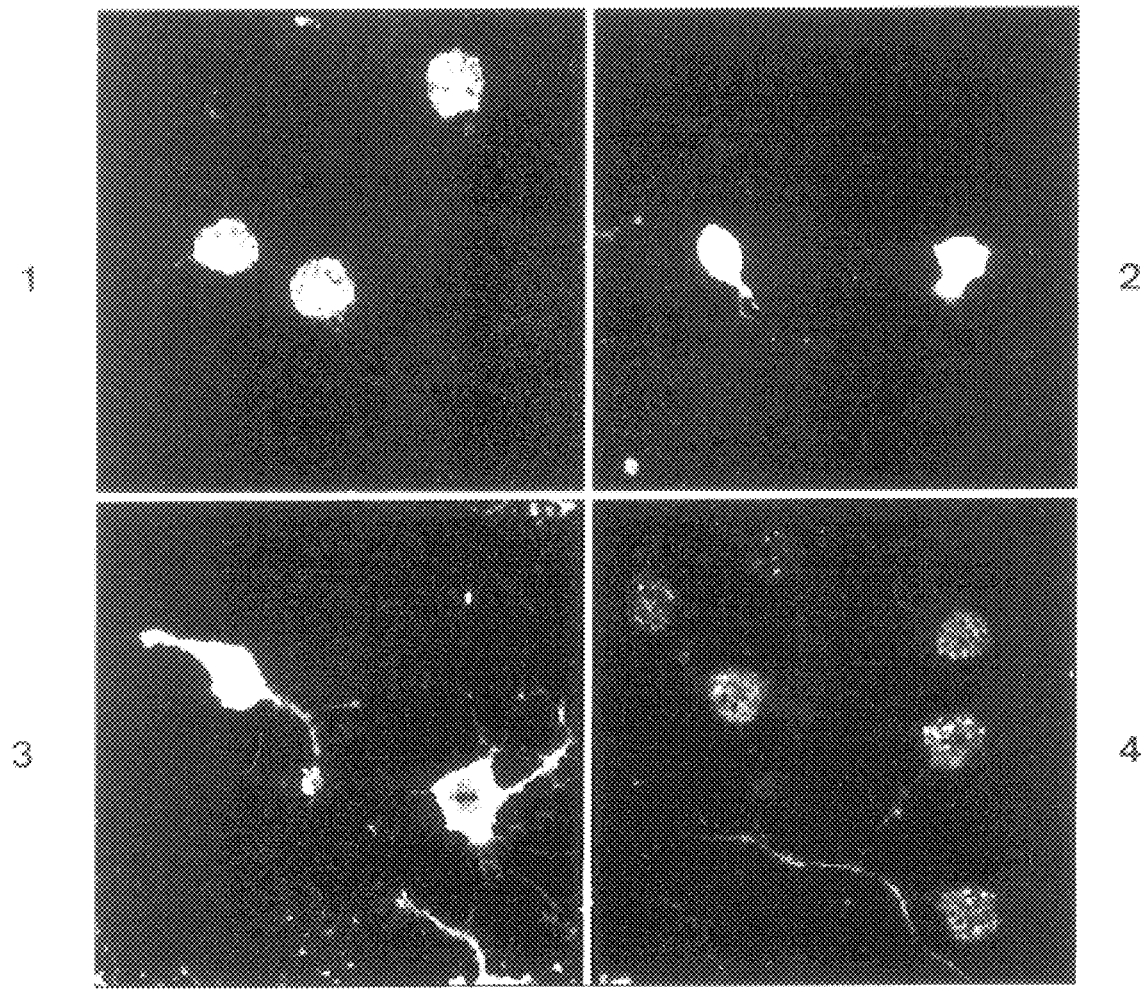
FIG. 6 demonstrates the confocal microscopy cell images of the cells that are incubated at 37° C. with peptides Met-Arg, W/R, and L/R.

Legend to FIG. 6:

1: peptide 7Arg
2: peptide Met-Arg
3: peptide W/R
4: peptide L/R.

Internalization and cytoplasmic and nuclear addressing of Met-Arg, of 7Arg and of W/R are observed. However, the peptide L/R is found in a fraction which is apparently of the vesicular type, probably of endocytic character.

CONCLUSION

The results obtained with the peptides of Table I make it possible to conclude that:

internalization does not require a receptor since the peptides 58-43 and 43-58D are internalized. However, the first has a sequence which is different from that of the initial peptide (even if its general amphiphilic helical structure is conserved), and the peptide consisting of amino acids of the D series should not interact with a natural receptor composed of amino acids of the L series;

the alpha-helix structure is not necessary since the introduction of a proline and a fortiori of 3 destroys the helicity. However, it is noted that the addition of prolines may interfere with the nuclear addressing.

As regards the peptides of Table II, it may be concluded from the results obtained that:

the amphiphilicity is necessary for internalization, but it is not sufficient since L/R does not have the properties of W/R the presence and the position of Trp residues are important.

Since the inventors have also demonstrated the internalization of the homeodomain of the Engrailed homeoprotein, which does not have the Trp residue in 56 (which is replaced by an Ile residue) but has conserved that in 48, it can be concluded therefrom that only Trp 48 is important for translocation.

What is claimed is:

1. A process of transporting into a living cell a molecule comprising, linking said molecule to a peptidic vector comprising of a peptide having an amino acid sequence represented by formula (I)

$$NH_2-X_1-X_2-X_3-X_4-X_5-X_6-X_7-X_8-X_9-X_{10}-X_{11}-X_{12}-X_{13}-X_{14}-X_{15}-X_{16}-COOH$$

or formula (Ia)

$$NH_2-X_{16}-X15-X_{14}-X_{13}-X_{12}-X_{11}-X_{10}-X_9-X_8-X_7-X_6-X_5-X_4-X_3-X_2-X_1-COOH$$

wherein (a) $X_1, X_2, X_3, X_4, X_5, X_6, X_7, X_8, X_9, X_{10}, X_{11}, X_{12}, X_{13}, X_{14}, X_{15}$, and $X_{16}$ each represents an α-amino acid, from 6 to 10 of which are hydrophobic amino acids;

(b) $X_6$ represents tryptophan;

(c) $X_3$ and $X_5$ are not both valine in the same sequence; and (d) formula (I) and formula (Ia) do not represent a peptide having a sequence of SEQ ID NO:1; and contacting said living cell with said peptidic vector with said molecule linked thereto, whereby said molecule is carried across membranes of the living cell.

2. A process according to claim 1, wherein said molecule is a peptide.

3. A process according to claim 1, wherein said molecule is oligonucleotide sequence.

4. A process according to claim 1, wherein said peptidic vector comprises 6 hydrophobic amino acids and 10 non-hydrophobic amino acids.

5. A process according to claim 1, wherein said peptidic vector comprises alternating stretches of from 1 to 6 non-hydrophobic amino acids and from 1 to 6 hydrophobic amino acids.

6. A process according to claim 1, wherein $X_1, X_2, X_4, X_9, X_{15}$, and $X_{16}$ are non-hydrophobic amino acids, and $X_3, X_7$, and $X_{14}$ are hydrophobic amino acids.

7. A process according to claim 1, wherein $X_{14}$ represents tryptophan or isoleucine.

8. A process according to claim 1, wherein at least one of the amino acids in positions $X_3, X_7$, and $X_{14}$ is a proline.

9. A peptidic vector for transporting a molecule into a living cell comprising a peptide having an amino acid sequence represented by formula (I)

$$NH_2-X_1-X_2-X_3-X_4-X_5-X_6-X_7-X_8-X_9-X_{10}-X_{11}-X_{12}-X_{13}-X_{14}-X_{15}-X_{16}-COOH$$

wherein, each of $X_1, X_2, X_3, X_4, X_5, X_6, X_7, X_8, X_9, X_{10}, X_{11}, X_{12}, X_{13}, X_{14}, X_{15}$, and $X_{16}$ represents an α-amino acid, from 6 to 10 of which being hydrophobic amino acids;

$X_1, X_2, X_4, X_9, X_{15}$, and $X_{16}$ are non-hydrophobic amino acids;

$X_3, X_7$, and $X_{14}$ are hydrophobic amino acids;

$X_6$ represents tryptophan;

$X_3$ and $X_5$ are not both valine in the same sequence; and formula (I) does not represent a peptide having a sequence of SEQ ID NO:1.

10. The peptidic vector of claim 9, wherein $X_{14}$ represents tryptophan or isoleucine.

11. The peptidic vector of claim 9, wherein said vector comprises 6 hydrophobic amino acids and 10 non-hydrophobic amino acids.

12. The peptidic vector of claim 9, wherein said vector comprises alternating stretches of from 1 to 6 hydrophobic amino acids and from 1 to 6 non-hydrophobic amino acids.

13. The peptidic vector of claim 9, wherein said amino acid sequence is represented by a sequence selected from the group consisting of SEQ ID NO:4, SEQ ID NO:5, SEQ ID NO:6, SEQ ID NO:7, SEQ ID NO:8, and SEQ ID NO:9.

14. A transport system for transporting a molecule into a living cell, comprising said molecule bound to the peptidic vector according claim 13.

15. A transport system for transporting a molecule into a living cell, comprising said molecule bound to the peptidic vector according claim 9.

16. The transport system of claim 15, wherein said molecule is a protein or peptide.

17. The transport system of claim 15, wherein said molecule is a non-peptidic active molecule.

18. A peptidic vector for transporting a molecule into a living cell comprising a peptide having an amino acid sequence represented by formula (Ia)

$$NH_2-X_{16}-X_{15}-X_{14}-X_{13}-X_{12}-X_{11}-X_{10}-X_9-X_8-X_7-X_6-X_5-X_4-X_3-X_2-X_1-COOH$$

wherein, each of $X_1, X_2, X_3, X_4, X_5, X_6, X_7, X_8, X_9, X_{10}, X_{11}, X_{12}, X_{13}, X_{14}, X_{15}$, and $X_{16}$ represents an α-amino acid, from 6 to 10 of which being hydrophobic amino acids;

$X_1, X_4, X_{15}$, and $X_{16}$ are Lys or Arg;

$X_2$ is Gln or Arg;

$X_9$ is Asn or Arg;

$X_3$ and $X_{14}$ are Ile or Trp;

$X_6$ is Trp; and $X_7$ is Phe or Trp.

19. The peptidic vector of claim 18, wherein said amino acid sequence is represented by SEQ ID NO:3 or SEQ ID NO:9.

20. A transport system for transporting a molecule into a living cell, comprising said molecule bound to the peptidic vector according claim 19.

21. A transport system for transporting a molecule into a living cell, comprising said molecule bound to the peptidic vector according claim 18.

22. A transporting system for transporting a non-peptidic active molecule into a living cell, comprising:

the active molecule to be transported linked to a peptidic vector, said peptidic vector comprising of a peptide having an amino acid sequence represented by formula (I)

$$NH_2-X_1-X_2-X_3-X_4-X_5-X_6-X_7-X_8-X_9-X_{10}-X_{11}-X_{12}-X_{13}-X_{14}-X_{15}-X_{16}-COOH$$

or formula (Ia)

$$NH_2-X_{16}-X_{15}-X_{14}-X_{13}-X_{12}-X_{11}-X_{10}-X_9-X_8-X_7-X_6-X_5-X_4-X_3-X_2-X_1-COOH$$

wherein (a) $X_1, X_2, X_3, X_4, X_5, X_6, X_7, X_8, X_9, X_{10}, X_{11}, X_{12}, X_{13}, X_{14}, X_{15}$, and $X_{16}$ each represents an α-amino acid, from 6 to 10 of which are hydrophobic amino acids;

(b) $X_6$ represents tryptophan;

(c) $X_3$ and $X_5$ are not both valine in the same sequence; and (d) formula (I) and formula (Ia) do not represent a peptide having a sequence of SEQ ID NO:1.

23. The transport system of claim 22, wherein said active molecule is an oligonucleotide.

24. The transport system of claim 22, wherein said peptidic vector comprises 6 hydrophobic amino acids and 10 non-hydrophobic amino acids.

25. The transport system of claim 22, wherein, in said peptidic vector, at least one of the amino acids in positions $X_3$, $X_7$, and $X_{14}$ is a proline.

* * * * *

UNITED STATES PATENT AND TRADEMARK OFFICE
CERTIFICATE OF CORRECTION

PATENT NO.    : 6,080,724
DATED         : June 27, 2000
INVENTOR(S)   : Chassaing et al.

It is certified that error appears in the above-identified patent and that said Letters Patent is hereby corrected as shown below:

<u>Title page,</u>
Item [56] References Cited, OTHER PUBLICATIONS, "9120-9194" should read -- 9120-9124 --.

<u>Column 13,</u>
Line 4, after "comprising" cancel "of";
Line 12, "X15" should read -- $X_{15}$ --;
Line 52, "X, $_{x2}$," should read -- $X_1$, $X_2$, --.

Signed and Sealed this

Twenty-first Day of May, 2002

Attest:

JAMES E. ROGAN
Attesting Officer    Director of the United States Patent and Trademark Office

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 16 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO: 1:

-continued

```
Arg Gln Ile Lys Ile Trp Phe Gln Asn Arg Arg Met Lys Trp Lys Lys
1               5                   10                  15
```

(2) INFORMATION FOR SEQ ID NO: 2:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 2:

```
Thr Glu Arg Gln Ile Lys Ile Trp Phe Gln Asn Arg Arg Met Lys
1               5                   10                  15
```

(2) INFORMATION FOR SEQ ID NO: 3:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 3:

```
Lys Lys Trp Lys Met Arg Arg Asn Gln Phe Trp Ile Lys Ile Gln Arg
1               5                   10                  15
```

(2) INFORMATION FOR SEQ ID NO: 4:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION:1..16
        (D) OTHER INFORMATION:/product= "amino acids of the D series"

(xi) SEQUENCE DESCRIPTION: SEQ ID NO: 4:

```
Arg Gln Ile Lys Ile Trp Phe Gln Asn Arg Arg Met Lys Trp Lys Lys
1               5                   10                  15
```

(2) INFORMATION FOR SEQ ID NO: 5:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 5:

```
Arg Gln Ile Lys Ile Trp Phe Pro Asn Arg Arg Met Lys Trp Lys Lys
1               5                   10                  15
```

```
(2) INFORMATION FOR SEQ ID NO: 6:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 6:

Arg Gln Pro Lys Ile Trp Phe Pro Asn Arg Arg Lys Pro Trp Lys Lys
1               5                   10                  15

(2) INFORMATION FOR SEQ ID NO: 7:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 7:

Arg Gln Ile Lys Ile Trp Phe Gln Asn Met Arg Lys Trp Lys Lys
1               5                   10                  15

(2) INFORMATION FOR SEQ ID NO: 8:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 8:

Arg Gln Ile Lys Ile Trp Phe Gln Asn Arg Arg Met Arg Trp Arg Arg
1               5                   10                  15

(2) INFORMATION FOR SEQ ID NO: 9:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 9:

Arg Arg Trp Arg Arg Trp Trp Arg Arg Trp Trp Arg Arg Trp Arg Arg
1               5                   10                  15

(2) INFORMATION FOR SEQ ID NO: 10:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 10:

Arg Leu Arg Arg Leu Leu Arg Arg Leu Leu Arg Arg Leu Arg Arg
1               5                   10                  15
```